United States Patent [19]
Broglie et al.

[11] Patent Number: 5,994,623
[45] Date of Patent: Nov. 30, 1999

[54] CORN 4-α-GLUCANOTRANSFERASE

[75] Inventors: Karen E. Broglie, Landenberg, Pa.; Enno Krebbers, Ardentown, Del.

[73] Assignee: E. I. du Pont de Nemours and Company, Wilmington, Del.

[21] Appl. No.: 08/838,543

[22] Filed: Apr. 9, 1997

[51] Int. Cl.⁶ .............................. C12N 15/29; C12N 5/04; C12N 15/84; A01H 4/00
[52] U.S. Cl. ...................... 800/278; 536/23.6; 435/419; 435/69.1; 435/172.3
[58] Field of Search .......................... 536/23.6; 435/419, 435/69.1, 172.3; 800/205, DIG. 56

[56] References Cited

U.S. PATENT DOCUMENTS

| | | | |
|---|---|---|---|
| 4,945,050 | 7/1990 | Sanford et al. | 435/172.1 |
| 5,107,065 | 4/1992 | Shewmaker et al. | 800/205 |
| 5,231,020 | 7/1993 | Jorgensen et al. | 435/172.3 |
| 5,561,236 | 10/1996 | Leemans et al. | 800/205 |
| 5,646,024 | 7/1997 | Leemans et al. | 435/172.3 |

OTHER PUBLICATIONS

Matzke and Matzke. Plant Physiol. 1995. vol. 107: 679–685.
Finnegan and McElory. Bio/Technology. 1994. vol. 12: 883–888.
Carvalho et al. The EMBO Journal. 1992. vol. 11: 5995–5602).
Potrykus I. Ann review of Plant Physiol. 1991. vol. 42: 205–225.
Ejdeback et al. Protein Expression and Purification. 1997. vol. 11: 17–25.
Mehta et al. Protein Expression and Purification. 1997. vol. 11: 86–94.
Tahaka et al. The Journal of Biological Chemistry. 1993. vol. 268(2). 1391–1396.
Preiss, J., (1988) Biochemistry of Plants 14:181–253.
Walker, C.E., (1988) Cereal Foods World 33:491–494.
Nucleic Acids Research 13:3021–3030 (1985).
Biochemical Journal 219 (No. 2):345–373 (1984).
Chu et al., (1975) Sci. Sin. Peking 18:659–668.
Deblaere et al., (1987) Meth. Enzymol. 153:277–292.
Hoheisel, J.D. et al., In Nonmammalian Genomic Analysis: A Practical Guide, Academic Press 1996, pp. 319–346.
Lander et al., (1987) Genomics 1:174–181.
Botstein, D. et al., (1980) Am. J. Hum. Genet. 32:314–331.
Bernatzky, R. and Tanksley S.D. (1986) Plant Mol. Biol. Reporter 4(1):37–41.
Okamuro and Goldberg, (1989) Biochemistry of Plants, 15:1–82.
Ingelbrecht et al., (1989) Plant Cell 1:671–680.
Raikhel, N. (1992) Plant Phys. 100:1627–1632.
Smith, A. et al., (1995) Plant Physiol. 107:673–677.
Turner, R. and Foster, G.D., (1995) Molecular Biotechnology 3:225.
Fromm et al., (1990) Bio/Technology 8:833–839.
Lerner, R.A., (1984) Adv. Immunol. 36:1 Maniatis.
Altschul, S.F. et al. (1990) J. Mol. Biol. 215:403–410.
Jones et al., (1985) Embo J. 4:2411–2418.
Hizukuri (1986) Carbohydrate Res. 147:342–347.
Odell et al., (1985) Nature 313:810–812.
De Almeida et al., (1989) Mol. Gen. Genetics 218:78–86.
Loh et al., (1989) Science 243:217.
Klein et al., (1987) Nature (London) 327:70–73.
Ohara et al., (1989) PNAS USA 86:5673.
Frohman et al., (1988) PNAS USA 85:8998.
Chrispeels, J.J., (1991) Ann. Rev. Plant Phys. Plant Mol Biol. 42:21–53.

(List continued on next page.)

*Primary Examiner*—Douglas W. Robinson
*Assistant Examiner*—Ousama M-Faiz Zaghmout

[57] ABSTRACT

This invention relates to isolated nucleic acid fragments encoding all or a substantial portion of a corn 4-α-glucanotransferase. The invention also relates to the construction of chimeric genes encoding all or a portion of a corn 4-α-glucanotransferase, in sense or antisense orientation, wherein expression of the chimeric gene results in production of altered levels of corn 4-α-glucanotransferase in a transformed host cell.

8 Claims, 3 Drawing Sheets

OTHER PUBLICATIONS

Takaha et al., J. Biol. Chem., (1993) 268:1391–1396.
Ong, Carbohydrate Res., (1994) 260:99–117.
Mol. Microbiol., vol. 2(4). Pugsley et al., 1988, pp. 473–479.
Cell, vol. 31(2), Lacks, 1982, pp. 327–336.
EMBL Accession X68664.
Genbank Accession M32793.
Genbank Accession L45989.
Genbank Accession J01796.

FIG. 1

```
                       250       260       270       280       290       300       310       320
M32793         DHEKITF-RAPKAYPEQSMAVAATHDLPTLR----------GYWEGDLT-----------------LGKTLGLYPDEVV-LR 213
L45989         QRNGEF-PRISDYPRNAYATIGIHDVPSLQ-----------SFWHCRDLE---------------LFNQLGILNGEV--LK 211
J01796         --------------------------------------------------------AVKEELGELNIIAEDLGFMIDEVIELR 148
X68664         --------------------------------------------------------AILQAVGKINILAEDLGVTTEDVQLR 148
cs1.pk0030.g12 EDSIKFYPRFNLEDISSFRDLDEHSKNILRRLYNYYFVRQENLMRQNALKTLPVLNSSIMLACGEDLGLIPACVHPVM 314

330       340       350       360       370       380       390       400
M32793         GLYQDRELAKQGL--LDALHKYGCLPKRAGHKASLMSMIPTLNRGLQRY--------------------------------- 261
L45989         QKYDQRVMDKQAL--LNSLHRDNYLPPHYEGDALSMAMHDYLNRMHYY--------------------------------- 259
J01796         ERIGFPGMKILQFAFNPEDESIDSPHLAPANSVMYIGIHDNIVLGWYRNEIDDATREYMARYINRKEYE---------TVV 221
X68664         KSIEAPGMAVLQFAFGSDAENPHLPHNHEQNQVVYTGIHDDTIRGM-WDTLPQEEKSNVLKYLSNIEEE--------EIS 220
cs1.pk0030.g12 QEIGLIGLRIQRMPSEPNLE-FGIPSQYSYMTVCAPSCHDCSTLRAW-WEE-DEGRRSRFYKIVGSDEEPPSRCTPEVV 391

410       420       430       440       450       460       470       480
M32793         ------IADSNSALLGQPEEMLDMAEPVN-----------IPGTSYQYKMWRRKLSATLESMFADGVNKLLKDLDR--RRR 324
L45989         ------LAESNSRLIGVQLENLLSQEISFN-----------LPSTSNEYPMWCKKLAQPLAFTFSNEALKTFFVQINQ--GRN 322
J01796         HAMLRIVFSSVSFMAIATMQDLIELDE-----------AARMNFPSTLGGMWSMRMI-----EDQLTP-AVEEGLLDLTTIYRRI 289
X68664         RGLIEGAVSSVARIAITPMQDVLGLGS-----------DSRMNIPATQFGMWSWRIP----SS----TSFDNLDAFAKKL 281
cs1.pk0030.g12 HFIVQQHFDAPSMWAIFPLQDLIALKDKYTTRPAPEETINDPTNPKHYWRFRVHVTLESLINDKDIQATIKDLVTSSGRS 471
```

FIG. 1 (CONTINUED)

```
                          490          500
M32793           AAAKKK                           330
L45989           V                                323
J01796           ------------NENLVDL---KK         298
X68664           ------------RDILATY---GRL        291
cs1.pk0030.g12   FPGKKAEGADESGEKLSKVQLNGKA        496
```

FIG. 1 (CONTINUED)

CORN 4-α-GLUCANOTRANSFERASE

FIELD OF THE INVENTION

This invention is in the field of plant molecular biology. More specifically, this invention pertains to nucleic acid fragments encoding enzymes involved in starch biosynthesis in corn plants and seeds.

BACKGROUND OF THE INVENTION

Corn starch is an important component of food, feed, and industrial products. Broadly speaking, it consists of two types of glucan polymers: relatively long chained polymers with few branches known as amylose, and shorter chained but highly branched molecules called amylopectin. Its biosynthesis depends on the complex interaction of multiple enzymes (Smith, A. et al., (1995) *Plant Physiol.* 107:673–677; Preiss, J., (1988) *Biochemistry of Plants* 14:181–253). Chief among these are ADP-glucose pyrophosphorylase, which catalyzes the formation of ADP-glucose; a series of starch synthases which use ADP glucose as a substrate for polymer formation using a-1–4 linkages; and several starch branching enzymes, which modify the polymer by transferring segments of polymer to other parts of the polymer using a-1–6 linkages, creating branched structures. However, based on data from other starch forming plants such as potato, and on corn mutants, it is becoming clear that other enzymes also play a role in the determination of the final structure of starch. In particular, debranching and disproportionating enzymes not only participate in starch degradation, but also in modification of starch structure during its biosynthesis. Different models for this action have been proposed, but all share the concept that such activities, or lack thereof, change the structure of the starch produced.

This is of applied interest because changes in starch structure, such as the relative amounts of amylose and amylopectin or the degree and length of branching of amylopectin, alter its function in cooking and industrial processes. For example, starch derived from different naturally occurring mutants of corn can be shown on the one hand to differ in structure and correspondingly to differ in functional assays such as Rapid Visco analysis, which measures changes in viscosity as starch is heated and then cooled (Walker, C. E., (1988) *Cereal Foods World* 33:491–494). The interplay of different enzymes to produce different structures, and in turn how different structures correlate with different functionalities, is not yet completely understood. However, it is understood that changing starch structure will result in alteration in starch function which can in turn lead to new applications or reduced processing costs (certain starch functionalities can at present only be attained through expensive chemical modification of the starch).

The role of corn 4-α-glucanotransferase (EC 2.4.1.25; also known as "disproportionating enzyme") in starch biosynthesis, in particular in affecting the degree of branching, indicates that over-expression or reduction of expression of such genes in corn could be used to alter branch chain distribution of corn starch. While 4-α-glucanotransferase genes have been described from other plants (Takaha et al., (1993) *J. Biol. Chem.* 268:1391–1396), a 4 α-glucanotransferase gene has yet to be described for corn.

SUMMARY OF THE INVENTION

The instant invention relates to isolated nucleic acid fragments encoding a corn 4-α-glucanotransferase. In addition, this invention relates to nucleic acid fragments that are complementary to nucleic acid fragments encoding a corn 4-α-glucanotransferase.

In another embodiment, the instant invention relates chimeric genes encoding a corn 4-α-glucanotransferase or nucleic acid fragments that are complementary to nucleic acid fragments encoding a corn 4-α-glucanotransferase, operably linked to suitable regulatory sequences, wherein expression of the chimeric gene results in production of altered levels of corn 4-α-glucanotransferase in a transformed host cell.

In a further embodiment, the instant invention concerns a transformed host cell comprising in its genome a chimeric gene encoding a corn 4-α-glucanotransferase, operably linked to suitable regulatory sequences, wherein expression of the chimeric gene results in production of altered levels of corn 4-α-glucanotransferase in the transformed host cell. The transformed host cells can be of eukaryotic or prokaryotic origin, and include cells derived from higher plants and microorganisms. The invention also includes transformed plants that arise from transformed host cells of higher plants, and from seeds derived from such transformed plants.

An additional embodiment of the instant invention concerns a method of altering the level of expression of corn 4-α-glucanotransferase in a transformed host cell comprising: a) transforming a host cell with the chimeric gene encoding a corn 4-α-glucanotransferase, operably linked to suitable regulatory sequences; and b) growing the transformed host cell under conditions that are suitable for expression of the chimeric gene wherein expression of the chimeric gene results in production of altered levels of corn 4-α-glucanotransferase in the transformed host cell.

An addition embodiment of the instant invention concerns a method for obtaining a nucleic acid fragment encoding all or substantially all of an amino acid sequence encoding a plant 4-α-glucanotransferase.

BRIEF DESCRIPTION OF THE DRAWINGS AND SEQUENCE DESCRIPTIONS

The invention can be more fully understood from the following detailed description and the accompanying drawings and the sequence descriptions which form a part of this application.

FIG. 1 shows a comparison of the amino acid sequences of *E. coli* (M32793), *H. influenzae* (L45989) and *S. pneumoniae* (J01796) 4-α-glucanotransferase enzymes, a potato 4-α-glucanotransferase enzyme (X69664), and the instant corn 4-α-glucanotransferase enzyme (cs1.pk0030.g12).

SEQ ID NO:1 is the nucleotide sequence of a cloned cDNA encoding a corn 4-α-glucanotransferase.

SEQ ID NO:2 is the deduced amino acid sequence of the cloned cDNA encoding a corn 4-α-glucanotransferase.

SEQ ID NO:3 is that portion of the amino acid sequence encoding the *E. coli* 4-α-glucanotransferase having Genbank accession No. M32793 that aligns with the instant corn 4-α-glucanotransferase.

SEQ ID NO:4 is that portion of the amino acid sequence encoding the *H. influenzae* 4-α-glucanotransferase having Genbank accession No. L45989 that aligns with the instant corn 4-α-glucanotransferase.

SEQ ID NO:5 is that portion of the amino acid sequence encoding the *S. pneumoniae* 4-α-glucanotransferase having Genbank accession No. J01796 that aligns with the instant corn 4-α-glucanotransferase.

SEQ ID NO:6 is that portion of the amino acid sequence encoding the potato 4-α-glucanotransferase having EMBL accession No. X69664 that aligns with the instant corn 4-α-glucanotransferase.

The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript vis-a-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less that the entire coding region of a gene, and by nucleic acid fragments that do not share 100% identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1× SSC, 0.1% SDS, 65° C.), with the sequences exemplified herein. Preferred substantially similar nucleic acid fragments of the instant invention are those nucleic acid fragments whose DNA sequences are 80% identical to the DNA sequence of the nucleic acid fragments reported herein. More preferred nucleic acid fragments are 90% identical to the identical to the DNA sequence of the nucleic acid fragments reported herein. Most preferred are nucleic acid fragments that are 95% identical to the DNA sequence of the nucleic acid fragments reported herein.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the corn 4-α-glucanotransferase protein as set forth in SEQ ID NO:2. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020). "Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propetides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Maniatis").

A corn 4-α-glucanotransferase gene has been isolated and identified by comparison of random plant cDNA sequences to the GenBank database using the BLAST algorithms well known to those skilled in the art. The nucleotide sequence of a corn 4-α-glucanotransferase cDNA is provided in SEQ ID NO:1, and the deduced amino acid sequence is provided in SEQ ID NO:2. 4-α-Glucanotransferase genes from other plants can now be identified by comparison of random cDNA sequences to the corn 4-α-glucanotransferase sequences provided herein.

The nucleic acid fragments of the instant invention may be used to isolate cDNAs and genes encoding homologous 4-α-glucanotransferases from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, other 4-α-glucanotransferase genes, either as cDNAs or genomic DNAs, could be isolated directly by using all or a portion of the instant corn 4-α-glucanotransferase gene as a DNA hybridization probe to screen libraries from any desired plant employing methodology well known to those skilled in the art. Specific oligonucleotide probes based upon the instant 4-α-glucanotransferase sequence can be designed and synthesized by methods known in the art (Maniatis). Moreover, the entire sequence can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequence. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous 4-α-glucanotransferase genes from DNA or RNA. The polymerase chain reaction may also be performed on a library of cloned nucleic acid fragments wherein the sequence of one primer is derived from the instant nucleic acid fragment, and the sequence of the other primer takes advantage of the presence of the polyadenylic acid tracts to the 3' end of the mRNA precursor encoding plant 4-α-glucanotransferase. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Finally, availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which corn 4-α-glucanotransferase is present at higher or lower levels than normal or in cell types or developmental stages in which it is not normally found. This would have the effect of altering starch structure in those cells.

Overexpression of corn 4-α-glucanotransferase may be accomplished by first constructing a chimeric gene in which the corn 4-α-glucanotransferase coding region is operably linked to a promoter capable of directing expression of a gene in the desired tissues at the desired stage of development. For reasons of convenience, the chimeric gene may comprise a promoter sequence and translation leader sequence derived from the same gene. 3' Non-coding sequences encoding transcription termination signals must also be provided. The instant chimeric genes may also comprise one or more introns in order to facilitate gene expression.

A plasmid vector comprising the instant chimeric gene is then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the 4-α-glucanotransferase protein to different cellular compartments, or to facilitate its secretion from the cell. It is thus envisioned that the chimeric gene described above may be further supplemented by altering the coding sequence to encode 4-α-glucanotransferase protein with appropriate intracellular targeting sequences such as transit sequences, signal sequences, or sequences encoding endoplasmic reticulum or nuclear localization signals added and/or with targeting sequences that are already present removed. While the references cited give examples of each of these, the list is not exhaustive and more targeting signals of utility may be discovered in the future. It may also be desirable to reduce or eliminate expression of the 4-α-glucanotransferase gene in plants for some applications. In order to accomplish this, a chimeric gene designed for co-suppression of 4-α-glucanotransferase can be constructed by linking the 4-α-glucanotransferase gene or gene fragment to a plant promoter sequences. Alternatively, a chimeric gene designed to express antisense RNA for all or part of the 4-α-glucanotransferase gene can be constructed by linking the 4-α-glucanotransferase gene or gene fragment in reverse orientation to a plant promoter sequences. Either the co-suppression or antisense chimeric gene could be introduced into plants via transformation wherein expression of the endogenous 4-α-glucanotransferase gene is reduced or eliminated.

Corn 4-α-glucanotransferase protein produced in heterologous host cells, particularly in the cells of microbial hosts, can be used to prepare antibodies to the protein by methods well known to those skilled in the art. The antibodies are useful for detecting corn 4-α-glucanotransferase protein in situ in cells or in vitro in cell extracts. Preferred heterologous host cells for production of corn 4-α-glucanotransferase protein are microbial hosts. Microbial expression systems and expression vectors containing regulatory sequences that direct high level expression of foreign proteins are well known to those skilled in the art. Any of these could be used to construct chimeric genes for production of corn 4-α-glucanotransferase. These chimeric genes could then be introduced into appropriate microorganisms via transformation to provide high level expression of corn 4-α-glucanotransferase. An example of a vector for high level expression of corn DP in a bacterial host is provided (Example 4).

All or a portion of the nucleic acid fragments of the instant invention may also be used as probes for genetically and physically mapping the genes that they are a part of, and as markers for traits linked to expression of corn 4-α-glucanotransferase. Such information may be useful in corn breeding in order to develop lines with desired starch phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980)*Am.J.Hum.Genet.* 32:314–331).

The production and use of plant gene-derived probes for use in genetic mapping is described in R. Bernatzky, R. and Tanksley, S. D. (1986) *Plant Mol.Biol.Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping. Although current methods of FISH mapping favor use of large clones (several to several hundred KB), improvements in sensitivity may allow performance of FISH mapping using shorter probes.

A variety of nucleic acid amplification-based methods of genetic and physical mapping may be carried out using the instant nucleic acid sequences. Examples include allele-specific amplification, polymorphism of PCR-amplificed fragments (CAPS), allele-specific ligation, nucleotide extension reactions, Radiation Hybrid Mapping and Happy Mapping. For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, this is generally not necessary for mapping methods. Such information may be useful in corn breeding in order to develop lines with desired starch phenotypes.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1
Composition of a Corn cDNA Library; Isolation and Sequencing of cDNA Clones A cDNA library representing mRNAs from corn leaf sheath obtained from five week old *Zea mays* B73 corn plants was prepared. RNA was sent to Stratagene Cloning Systems (La Jolla, Calif.) for custom synthesis of a cDNA library in a Uni-ZAP™ XR vector. Conversion of the Uni-ZAP™ XR library into a plasmid library was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted corn cDNA sequences. Amplified insert DNAs were sequenced in dye-primer sequencing reactions; the resulting products were analyzed using a Perkin Elmer Model 377 fluorescent sequencer.

Example 2
Identification and Characterization of cDNA Clones

A cDNA encoding a corn 4-α-glucanotransferase was identified by conducting a BLAST (Basic Local Alignment Search Tool; Altschul, S. F., et al., (1993) J. Mol. Biol. 215:403–410; see also www.ncbi.nlm.nih.gov/BLAST/) search for similarity to sequences contained in the GenBank database. The corn cDNA sequences obtained in Example 1 were analyzed for similarity to all publicly available DNA sequences contained in the GenBank Database using the BLASTN algorithm provided by the National Center for Biotechnology Information (NCBI). The DNA sequences were translated in all reading frames and compared for similarity to all publicly available protein sequences contained in the GeneBank Database using the BLASTX algorithm provided by the NCBI.

Figure 1:
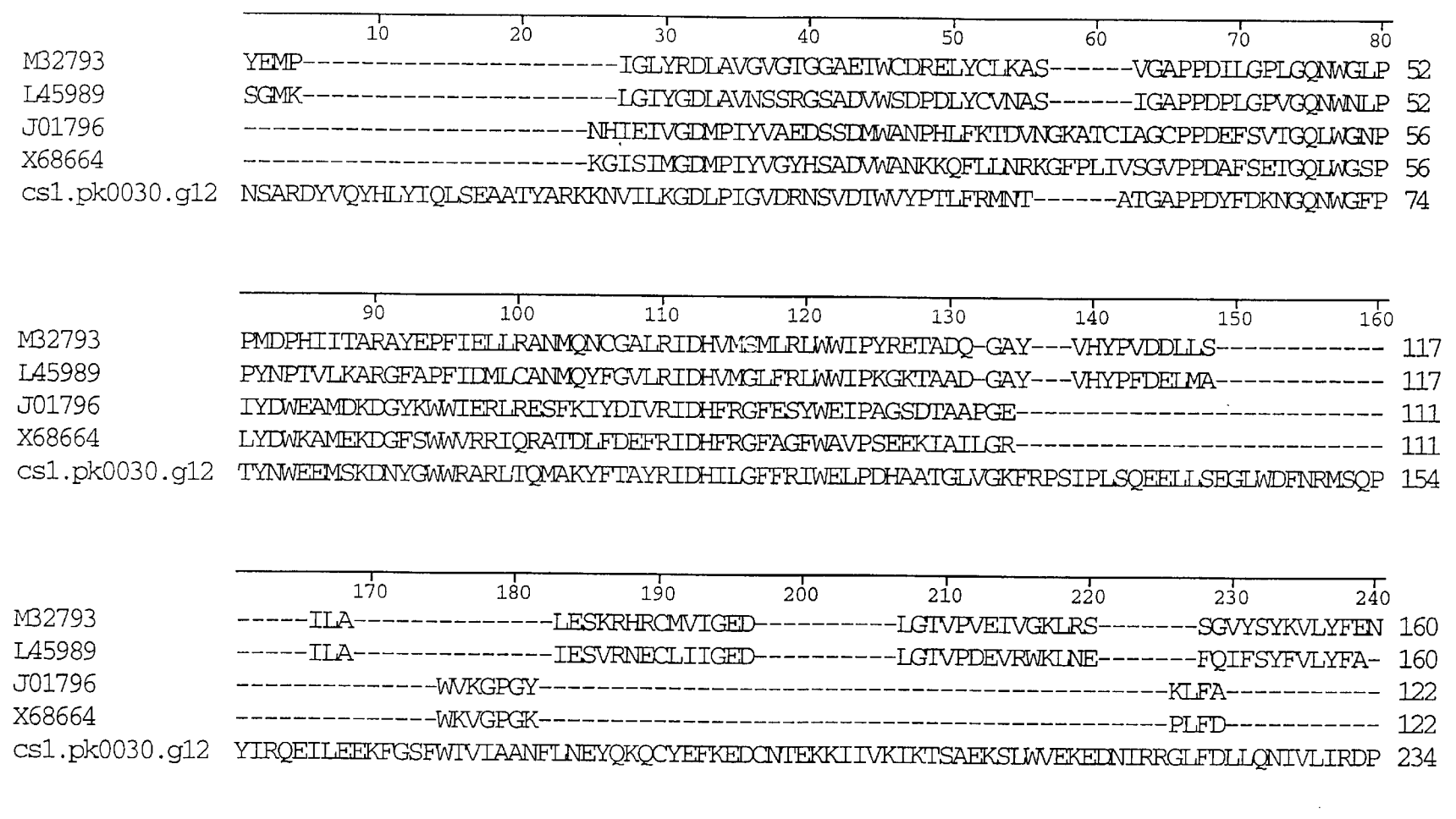

The BLASTX search using clone cs1.pk0030.g12 revealed similarity of the protein encoded by the cDNA to *E.* coli (GenBank Accession No. M32793; logP=6.47)), *H. influenzae* (GenBank Accession No. L45989; logP=12.49) and *S. pneumoniae* (GeneBank Accession No. J01796; logP=17.85) 4-α-glucanotransferase enzymes and potato 4-α-glucanotransferase enzyme (EMBL Accession No. X68664; logP=16.80) (FIG. 1). SEQ ID NO:1 shows the nucleotide sequence of the 4-α-glucanotransferase cDNA. The corresponding amino acid sequence of the 4-α-glucanotransferase protein is shown in SEQ ID NO:2. The amino acid sequence of the instant corn 4-α-glucanotransferase shows approximately 32, 36 and 50% sequence identity to the *E. coli, H. influenzae* and *S. pneumoniae* 4-α-glucanotransferase enzymes, respectively, and 42% sequence identity to the potato 4-α-glucanotransferase. Sequence alignments and BLAST scores and probabilities indicate that the instant nucleic acid fragment encodes a portion of a corn 4-α-glucanotransferase enzyme.

Example 3
Expression of Chimeric Genes in Plant Cells

A chimeric gene comprising a corn 4-α-glucanotransferase cDNA in sense orientation with respect to the maize 27 kD zein promoter that is located 5' to the corn 4-α-glucanotransferase fragment, and the 10 kD zein 3' end that is located 3' to the corn 4-α-glucanotransferase fragment, can be constructed. The corn 4-α-glucanotransferase fragment of this gene may be generated by polymerase chain reaction (PCR) of the cDNA clone comprising the corn 4-α-glucanotransferase using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a 100 uL volume in a standard PCR mix consisting of 0.4 mM of each oligonucleotide and 0.3 pM of target DNA in 10 mM Tris-HCl, pH 8.3, 50 mM KCl, 1.5 mM $MgCl_2$, 0.001% w/v gelatin, 200 mM dGTP, 200 mM dATP, 200 mM dTTP, 200 mM dCTP and 0.025 unit Amplitaq™ DNA polymerase. Reactions are carried out in a Perkin-Elmer Cetus Thermocycler™ for 30 cycles comprising 1 minute at 95° C., 2 minutes at 55° C. and 3 minutes at 72° C., with a final 7 minute extension at 72° C. after the last cycle. The amplified DNA is then digested with restriction enzymes NcoI and SmaI and fractionated on a 0.7% low melting point agarose gel in 40 mM Tris-acetate, pH 8.5, 1 mM EDTA. The appropriate band can be excised from the gel, melted at 68° C. and combined with a 4.9 kb NcoI-SmaI fragment of the plasmid pML103. Plasmid pML103 has been deposited under the terms of the Budapest Treaty at ATCC (American Type Culture Collection, 12301 Parklawn Drive, Rockville, Md. 20852), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, the corn 4-α-glucanotransferase cDNA fragment, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al., (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Starch extracted from single seeds obtained from corn plants transformed with the chimeric gene can then be analyzed. Seeds can be steeped in a solution containing 1.0% lactic acid and 0.3% sodium metabisulfite, pH 3.82, held at 52° C. for 22–24 h. Seeds are then drained, rinsed and homogenized individually in 8–9 mL of a solution of 100 mM NaCl. Five mL of toluene are added to each tube and vigorously shaken twice for 6 minutes using a paint mixer, and allowed to settle for 30 minutes. Two mL of 100 mM NaCl is sprayed onto the solution, allowed to settle for 30 minutes, and the protein-toluene layer is aspirated off. The toluene wash step is repeated. Twelve mL water is added and shaken in a paint shaker for 45 seconds. This solution is centrifuged for 10 minutes and the water is removed. The water wash is repeated, followed by a final wash with 12 mL of acetone. After shaking and centrifugation steps, the acetone is drained and allowed to evaporate for 1 h. Starch extracts are incubated in a 40° C. oven overnight.

Extracted starches can be enzymatically debranched as follows. Extracted starches (10 mg) from individual seeds are gelatinized in 2 mL water by heating to 115° C. for 0.5 h. Four units of isoamylase (Sigma) in 50 mM NaOAc buffer, pH 4.5, are added to each of the gelatinized starches and placed in a water bath at 45° C. for 2.5 h. Enzyme is inactivated by heating samples to 115° C. for 5 minutes. Each sample is filtered through a 0.45 micron filter, and placed into individual autosampler vials. Samples can be held at 45° C. until injection.

Fifty mL of debranched starch sample may then be injected and run through four columns (3×250 Å and 1×500 Å ultrahydrogel™; Waters) arranged in series at 45° C. and eluted with 50 mM NaOAc at a flow rate of 0.7 mL/min. An appropriate sampling interval is 65 minutes. A refractive index detector (Waters), integrator/plotter (Spectra-Physics) and computer can be used for sample detection, recording of retention times and chromatogram storage, respectively. Retention times of collected samples may then be compared to retention times of pullulan standards (380K, 100K, 23.7K, 5.8K, 728 and 180 mw).

Spectra-Physics software can be used to make any baseline corrections to the chromatogram including subtraction of a blank chromatogram. Spectra-Physics GPC-PC software can be used to enter molecular weights and retention times of pullulan standards. The data may be imported to Microsoft Excel for parsing and stripping of all data except molecular weight and area percent of the chromatogram. The remaining data can be used to determine branch chain distribution of the amylopectin using Jandel Scientific Peakfit software. A series of six Gaussian curves may be fit to the amylopectin portion of the chromatograms as described by Ong et al. ((1994) *Carbohydrate Res.* 260:99–117).

Amylopectin is typically described by its distribution of branch chains in the molecule. The amylopectin molecule is comprised of alternating crystalline and amorphous regions. The crystalline region is where many of the branch points (α-1,6 linkages) occur, while the amorphous region is an area of little to no branching and few branch chains. The type of chain may be designated as A or B. A chains are unbranched and span a single crystalline region. B1 chains also span a single crystalline region but are branched. B2, B3 and B4+ chains are branched and span 2, 3 and 4 or more crystalline regions, respectively (Hizukuri (1986) *Carbohydrate Res.* 147:342–347). The relative area under the six Gaussian curves fit to the amylopectin portion of the chromatograms using Peakfit software can be used to determine the area percentage of the A, B1, B2, B3 and B4+ chains. The areas of the first and second peaks can be summed to give the relative amount of A and B1 chains, the third and fourth peaks represent the B2 and B3 chains, respectively, and the sum of the fifth and sixth peaks represent the relative area of the B4+ chains.

Starches derived from kernels of plants transformed with the chimeric gene can also be tested for functionality by techniques well known to those skilled in the art. For example, starch can be extracted from dry mature kernels from transformed plants. Fifteen g of kernels are weighed into a 50 mL Erlenmeyer flask and steeped in 50 mL of steep solution (same as above) for 18 h at 52° C. The kernels are drained and rinsed with water. The kernels are then homogenized using a 20 mm Polytron probe (Kinematica GmbH; Kriens-Luzern, Switzerland) in 50 mL of cold 50 mM NaCl. The homogenate is filtered through a 72 micron mesh screen. The filtrate is brought up to a total volume of 400 mL with 50 mM NaCl and an equal volume of toluene is added. The mixture is stirred with a magnetic stir bar for 1 h at sufficient speed to completely emulsify the two phases. The emulsion is allowed to separate overnight in a covered beaker. The upper toluene layer is aspirated from the beaker and discarded. The starch slurry remaining in the bottom of the beaker is resuspended, poured into a 250 mL centrifuge bottle and centrifuged 15 minutes at 25,000 RCF. The supernatant is discarded and the starch is washed sequentially with water and acetone by shaking and centrifuging as above. After the acetone wash and centrifugation the acetone is decanted and the starch allowed to dry overnight in a fume hood at room temperature.

A Rapid Visco Analyzer (Newport Scientific; Sydney, Australia) with high sensitivity option and Thermocline software can then be used for pasting curve analyisis. For each line, 1.50 g of starch is weighed into the sample cup and 25 mL of phosphate/citrate buffer (pH 6.50) containing 1% NaCl was added. Pasting curve analysis can be performed using the following temperature profile: idle temperature 50° C., hold at 50° C. for 0.5 minutes, linear heating to 95° C. for 2.5 minutes, linear cooling to 50° C. over 4 minutes, hold at 50° C. for four minutes.

Results of the Rapid Visco Analyzer pasting analysis may demonstrate that the starch produced by lines transformed with the chimeric gene differ in its pasting properties both from normal dent starch. This result may demonstrate that the alteration of starch fine structure produced by altering expression of a corn 4-α-glucanotransferase can create a starch of novel functionality.

Example 4

Expression of Chimeric Genes in Microbial Cells

The corn 4-α-glucanotransferase cDNA can be inserted into the T7 *E. coli* expression vector pET24d (Novagen). Plasmid DNA containing the corn 4-α-glucanotransferase cDNA may be appropriately digested to release a nucleic acid fragment encoding the corn 4-α-glucanotransferase. This fragment may then be purified on a 1% NuSieve® GTG® low melting agarose gel (FMC®). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the corn 4-α-glucanotransferase fragment using T4 DNA ligase (NEB). The corn 4-α-glucanotransferase fragment containing the ligated adapters can be purified from the excess adapters using low melting agarose as described above. The vector pET24d is digested, dephosphorylated with alkaline phosphatase (NEB) and deproteinized with phenol/chloroform as described above. The prepared vector pET24d and corn 4-α-glucanotransferase fragment can then be ligated at 16° C. for 15 hours followed by transformation into DH5 electrocompetent cells (GIBCO BRL). Transformants can be selected on agar plates containing 2×YT media and 50 µg/mL kanamycin. Transformants containing the corn 4-α-glucanotransferase gene are then screened for the correct orientation with respect to pET24d T7 promoter by restriction enzyme analysis.

Clones in the correct orientation with respect to the T7 promoter can be transformed into BL21(DE3) competent cells (Novagen) and selected on 2×YT agar plates containing 50 µg/ml kanamycin. A colony arising from this transformation construct can be grown overnight at 30° C. in 2×YT media with 50 µg/mL kanamycin. The culture is then diluted two fold with fresh media, allowed to re-grow for 1 h, and induced by adding isopropyl-thiogalactopyranoside to 1 mM final concentration. Cells are then harvested by centrifugation after 3 h and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

What is claimed is:

1. An isolated nucleic acid fragment comprising a member selected from the group consisting of:
   (a) an isolated nucleic acid fragment encoding the amino acid sequence set forth in SEQ ID NO:2;
   (b) an isolated nucleic acid fragment that hybridizes under stringent conditions to an isolated nucleic acid fragment encoding the amino acid sequence set forth in SEQ ID NO:2; and
   (c) an isolated nucleic acid fragment that is complementary to (a) or (b).

2. The isolated nucleic acid fragment of claim 1 wherein the nucleotide sequence of the fragment is set forth in SEQ ID NO:1.

3. A chimeric gene comprising the nucleic acid fragment of claim 1 operably linked to suitable regulatory sequences.

4. A transformed host cell comprising the chimeric gene of claim 3.

5. A method of altering the level of expression of a corn 4-α-glucanotransferase in a host cell comprising:
   (a) transforming a host cell with the chimeric gene of claim 3; and
   (b) growing the transformed host cell produced in step (a) under conditions that are suitable for expression of the chimeric gene
wherein expression of the chimeric gene results in production of altered levels of a corn 4-α-glucanotransferase in the transformed host cell.

6. An isolated nucleic acid fragment encoding a plant 4-α-glucanotransferase that said isolated nucleic acid fragment obtained by a method comprising:
   (a) probing a cDNA or genomic library with the nucleic acid fragment of claim 1;
   (b) identifying a DNA clone that hybridizes at stringent conditions with the nucleic acid fragment of claim 1; and
   (c) sequencing the cDNA or genomic fragment that comprises the clone identified in step (c).

7. An isolated nucleic acid fragment encoding a plant 4-α-glucanotransferase that said isolated nucleic acid fragment obtained by a method comprising:
   (a) synthesizing an oligonucleotide primer corresponding to a portion of the sequence set forth in SEQ ID NO:1; and
   (b) amplifying a cDNA insert present in a cloning vector using the oligonucleotide primer of step (a) and a primer representing sequences of the cloning vector.

8. The isolated nucleic acid fragment of claim 1 wherein said isolated nucleic acid fragment encodes a functional transcript.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1683 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 2..1489

(xi) SEQUENCE DESCRIPTION: SEQ ID NO:1:

```
G AAT TCG GCA CGA GAC TAT GTT CAG TAC CAT CTA TAT ATA CAA TTA         46
  Asn Ser Ala Arg Asp Tyr Val Gln Tyr His Leu Tyr Ile Gln Leu
    1               5                  10                  15

TCT GAG GCA GCA ACA TAT GCA AGA AAG AAA AAT GTT ATC CTG AAA GGT       94
Ser Glu Ala Ala Thr Tyr Ala Arg Lys Lys Asn Val Ile Leu Lys Gly
                 20                  25                  30

GAT TTA CCT ATT GGT GTT GAT AGG AAT AGT GTC GAT ACA TGG GTA TAC      142
Asp Leu Pro Ile Gly Val Asp Arg Asn Ser Val Asp Thr Trp Val Tyr
             35                  40                  45

CCA ACC TTG TTT CGC ATG AAT ACC GCT ACT GGA GCG CCT CCT GAT TAT      190
Pro Thr Leu Phe Arg Met Asn Thr Ala Thr Gly Ala Pro Pro Asp Tyr
         50                  55                  60

TTT GAC AAG AAT GGA CAA AAT TGG GGT TTT CCT ACA TAT AAC TGG GAG      238
Phe Asp Lys Asn Gly Gln Asn Trp Gly Phe Pro Thr Tyr Asn Trp Glu
     65                  70                  75

GAG ATG TCA AAG GAT AAT TAT GGG TGG TGG CGA GCT CGT CTG ACA CAG      286
Glu Met Ser Lys Asp Asn Tyr Gly Trp Trp Arg Ala Arg Leu Thr Gln
 80                  85                  90                  95

ATG GCA AAG TAC TTC ACA GCA TAC AGG ATA GAC CAC ATC TTG GGT TTC      334
Met Ala Lys Tyr Phe Thr Ala Tyr Arg Ile Asp His Ile Leu Gly Phe
                100                 105                 110

TTT AGG ATA TGG GAG CTT CCA GAT CAT GCT GCA ACA GGT TTA GTT GGG      382
Phe Arg Ile Trp Glu Leu Pro Asp His Ala Ala Thr Gly Leu Val Gly
            115                 120                 125

AAA TTT AGA CCT TCC ATC CCT CTT AGT CAG GAG GAG CTT CTA AGT GAA      430
Lys Phe Arg Pro Ser Ile Pro Leu Ser Gln Glu Glu Leu Leu Ser Glu
```

-continued

```
                    130                 135                 140
GGT CTA TGG GAT TTT AAT CGG ATG AGC CAA CCA TAC ATT CGT CAG GAA           478
Gly Leu Trp Asp Phe Asn Arg Met Ser Gln Pro Tyr Ile Arg Gln Glu
145                 150                 155

ATA CTG GAG GAG AAG TTT GGA TCC TTT TGG ACA GTC ATT GCA GCC AAT           526
Ile Leu Glu Glu Lys Phe Gly Ser Phe Trp Thr Val Ile Ala Ala Asn
160                 165                 170                 175

TTT CTA AAT GAG TAC CAG AAG CAG TGT TAT GAG TTT AAA GAA GAT TGC           574
Phe Leu Asn Glu Tyr Gln Lys Gln Cys Tyr Glu Phe Lys Glu Asp Cys
                180                 185                 190

AAC ACA GAG AAA AAG ATT ATT GTA AAG ATT AAA ACA AGT GCT GAA AAG           622
Asn Thr Glu Lys Lys Ile Ile Val Lys Ile Lys Thr Ser Ala Glu Lys
            195                 200                 205

TCA CTG TGG GTA GAG AAA GAG GAC AAT ATC CGC CGT GGC CTT TTC GAT           670
Ser Leu Trp Val Glu Lys Glu Asp Asn Ile Arg Arg Gly Leu Phe Asp
        210                 215                 220

TTA CTA CAG AAT ATT GTC CTT ATC AGA GAT CCA GAG GAC TCC ACA AAA           718
Leu Leu Gln Asn Ile Val Leu Ile Arg Asp Pro Glu Asp Ser Thr Lys
225                 230                 235

TTC TAT CCC CGT TTC AAC CTG GAA GAC ACA TCA AGT TTT AGG GAC CTT           766
Phe Tyr Pro Arg Phe Asn Leu Glu Asp Thr Ser Ser Phe Arg Asp Leu
240                 245                 250                 255

GAT GAA CAC AGC AAA AAT ATC CTC AGA AGA TTG TAT TAT AAC TAT TAT           814
Asp Glu His Ser Lys Asn Ile Leu Arg Arg Leu Tyr Tyr Asn Tyr Tyr
                260                 265                 270

TTT GTT CGC CAA GAA AAT CTC TGG CGC CAA AAT GCC CTG AAG ACT TTG           862
Phe Val Arg Gln Glu Asn Leu Trp Arg Gln Asn Ala Leu Lys Thr Leu
            275                 280                 285

CCT GTC CTG CTG AAC TCG TCA GAT ATG TTA GCA TGT GGA GAG GAC CTT           910
Pro Val Leu Leu Asn Ser Ser Asp Met Leu Ala Cys Gly Glu Asp Leu
        290                 295                 300

GGC CTT ATC CCT GCT TGT GTT CAC CCT GTT ATG CAA GAA CTG GGG TTG           958
Gly Leu Ile Pro Ala Cys Val His Pro Val Met Gln Glu Leu Gly Leu
    305                 310                 315

ATT GGA TTG CGT ATC CAA AGA ATG CCT AGT GAA CCA AAC TTG GAA TTT          1006
Ile Gly Leu Arg Ile Gln Arg Met Pro Ser Glu Pro Asn Leu Glu Phe
320                 325                 330                 335

GGT ATT CCT TCT CAG TAT AGC TAT ATG ACG GTT TGT GCT CCC TCA TGT          1054
Gly Ile Pro Ser Gln Tyr Ser Tyr Met Thr Val Cys Ala Pro Ser Cys
                340                 345                 350

CAT GAC TGC TCT ACA TTA CGT GCT TGG TGG GAA GAA GAT GAA GGA AGA          1102
His Asp Cys Ser Thr Leu Arg Ala Trp Trp Glu Glu Asp Glu Gly Arg
            355                 360                 365

AGA AGT CGT TTC TAC AAG ACT GTA GTT GGC AGT GAT GAG GAG CCC CCA          1150
Arg Ser Arg Phe Tyr Lys Thr Val Val Gly Ser Asp Glu Glu Pro Pro
        370                 375                 380

TCT CGT TGC ACC CCG GAA GTA GTG CAC TTC ATT GTT CAG CAG CAT TTT          1198
Ser Arg Cys Thr Pro Glu Val Val His Phe Ile Val Gln Gln His Phe
    385                 390                 395

GAC GCT CCA TCA ATG TGG GCA ATC TTT CCA CTT CAG GAC CTC CTT GCA          1246
Asp Ala Pro Ser Met Trp Ala Ile Phe Pro Leu Gln Asp Leu Leu Ala
400                 405                 410                 415

CTG AAA GAC AAG TAC ACC ACA AGA CCA GCG CCA GAG GAA ACA ATC AAT          1294
Leu Lys Asp Lys Tyr Thr Thr Arg Pro Ala Pro Glu Glu Thr Ile Asn
                420                 425                 430

GAC CCC ACT AAC CCA AAG CAC TAT TGG AGA TTC CGT GTC CAC GTG ACA          1342
Asp Pro Thr Asn Pro Lys His Tyr Trp Arg Phe Arg Val His Val Thr
            435                 440                 445

TTG GAG TCC CTG CTG AAC GAC AAG GAC ATC CAG GCA ACC ATC AAG GAC          1390
Leu Glu Ser Leu Leu Asn Asp Lys Asp Ile Gln Ala Thr Ile Lys Asp
```

|   |   |   |   |   |   |   |   |   |   |   |   |   |   |   |   |
|---|---|---|---|---|---|---|---|---|---|---|---|---|---|---|---|
|   |   |   | 450 |   |   |   | 455 |   |   |   | 460 |   |   |   |   |
| CTG | GTC | ACA | AGC | AGT | GGG | AGG | TCC | TTC | CCC | GGA | AAG | AAG | GCG | GAA | GGT | 1438 |
| Leu | Val | Thr | Ser | Ser | Gly | Arg | Ser | Phe | Pro | Gly | Lys | Lys | Ala | Glu | Gly |
|   |   | 465 |   |   |   |   | 470 |   |   |   |   | 475 |   |   |   |

```
                                     450                  455                    460
CTG GTC ACA AGC AGT GGG AGG TCC TTC CCC GGA AAG AAG GCG GAA GGT                       1438
Leu Val Thr Ser Ser Gly Arg Ser Phe Pro Gly Lys Lys Ala Glu Gly
        465                 470                 475

GCC GAC GAG AGC GGG GAG AAG CTG TCC AAG GTG CAG CTG AAT GGT AAA                       1486
Ala Asp Glu Ser Gly Glu Lys Leu Ser Lys Val Gln Leu Asn Gly Lys
480                 485                 490                 495

GCT TAGGAAAGGA TTGCGAGAGC TGCTGGAAGT GACCACGGTT ACAAGTAAAT                            1539
Ala

AAATAGAATA AGGCGACAGA TTGCATCACC GTGTTGATCC AGGTGATGCT GTTTCTGGTA                     1599

GGAAATTCTT ACCCATGTGA TGTTCTTTCA ACTCTGGAAA TAAGAAGCAC CCTCTACCAA                     1659

GTCAGAAAGT GAAATAATCC ATCC                                                            1683

(2) INFORMATION FOR SEQ ID NO:2:

(i) SEQUENCE CHARACTERISTICS:
        (A) LENGTH:  496 amino acids
        (B) TYPE:  amino acid
        (D) TOPOLOGY:  linear (ii) MOLECULE TYPE:  protein (xi) SEQUENCE DESCRIPTION: SEQ ID NO:2:

Asn Ser Ala Arg Asp Tyr Val Gln Tyr His Leu Tyr Ile Gln Leu Ser
 1               5                  10                  15

Glu Ala Ala Thr Tyr Ala Arg Lys Lys Asn Val Ile Leu Lys Gly Asp
                20                  25                  30

Leu Pro Ile Gly Val Asp Arg Asn Ser Val Asp Thr Trp Val Tyr Pro
            35                  40                  45

Thr Leu Phe Arg Met Asn Thr Ala Thr Gly Ala Pro Pro Asp Tyr Phe
         50                  55                  60

Asp Lys Asn Gly Gln Asn Trp Gly Phe Pro Thr Tyr Asn Trp Glu Glu
 65                 70                  75                  80

Met Ser Lys Asp Asn Tyr Gly Trp Trp Arg Ala Arg Leu Thr Gln Met
                 85                  90                  95

Ala Lys Tyr Phe Thr Ala Tyr Arg Ile Asp His Ile Leu Gly Phe Phe
            100                 105                 110

Arg Ile Trp Glu Leu Pro Asp His Ala Ala Thr Gly Leu Val Gly Lys
        115                 120                 125

Phe Arg Pro Ser Ile Pro Leu Ser Gln Glu Glu Leu Leu Ser Glu Gly
    130                 135                 140

Leu Trp Asp Phe Asn Arg Met Ser Gln Pro Tyr Ile Arg Gln Glu Ile
145                 150                 155                 160

Leu Glu Glu Lys Phe Gly Ser Phe Trp Thr Val Ile Ala Ala Asn Phe
                165                 170                 175

Leu Asn Glu Tyr Gln Lys Gln Cys Tyr Glu Phe Lys Glu Asp Cys Asn
            180                 185                 190

Thr Glu Lys Lys Ile Ile Val Lys Ile Lys Thr Ser Ala Glu Lys Ser
        195                 200                 205

Leu Trp Val Glu Lys Glu Asp Asn Ile Arg Arg Gly Leu Phe Asp Leu
    210                 215                 220

Leu Gln Asn Ile Val Leu Ile Arg Asp Pro Glu Asp Ser Thr Lys Phe
225                 230                 235                 240

Tyr Pro Arg Phe Asn Leu Glu Asp Thr Ser Ser Phe Arg Asp Leu Asp
                245                 250                 255

Glu His Ser Lys Asn Ile Leu Arg Arg Leu Tyr Tyr Asn Tyr Tyr Phe
```

```
                260                 265                 270
Val Arg Gln Glu Asn Leu Trp Arg Gln Asn Ala Leu Lys Thr Leu Pro
                275                 280                 285

Val Leu Leu Asn Ser Ser Asp Met Leu Ala Cys Gly Glu Asp Leu Gly
                290                 295                 300

Leu Ile Pro Ala Cys Val His Pro Val Met Gln Glu Leu Gly Leu Ile
305                 310                 315                 320

Gly Leu Arg Ile Gln Arg Met Pro Ser Glu Pro Asn Leu Glu Phe Gly
                325                 330                 335

Ile Pro Ser Gln Tyr Ser Tyr Met Thr Val Cys Ala Pro Ser Cys His
                340                 345                 350

Asp Cys Ser Thr Leu Arg Ala Trp Trp Glu Glu Asp Glu Gly Arg Arg
                355                 360                 365

Ser Arg Phe Tyr Lys Thr Val Val Gly Ser Asp Glu Glu Pro Pro Ser
                370                 375                 380

Arg Cys Thr Pro Glu Val Val His Phe Ile Val Gln Gln His Phe Asp
385                 390                 395                 400

Ala Pro Ser Met Trp Ala Ile Phe Pro Leu Gln Asp Leu Leu Ala Leu
                405                 410                 415

Lys Asp Lys Tyr Thr Thr Arg Pro Ala Pro Glu Glu Thr Ile Asn Asp
                420                 425                 430

Pro Thr Asn Pro Lys His Tyr Trp Arg Phe Arg Val His Val Thr Leu
                435                 440                 445

Glu Ser Leu Leu Asn Asp Lys Asp Ile Gln Ala Thr Ile Lys Asp Leu
                450                 455                 460

Val Thr Ser Ser Gly Arg Ser Phe Pro Gly Lys Lys Ala Glu Gly Ala
465                 470                 475                 480

Asp Glu Ser Gly Glu Lys Leu Ser Lys Val Gln Leu Asn Gly Lys Ala
                485                 490                 495

(2) INFORMATION FOR SEQ ID NO:3:

(i) SEQUENCE CHARACTERISTICS:
        (A) LENGTH:  330 amino acids
        (B) TYPE:  amino acid
        (C) STRANDEDNESS:  single
        (D) TOPOLOGY:  linear (ii) MOLECULE TYPE:  peptide (xi) SEQUENCE DESCRIPTION:  SEQ ID NO:3:

Tyr Glu Met Pro Ile Gly Leu Tyr Arg Asp Leu Ala Val Gly Val Gly
1               5                   10                  15

Thr Gly Gly Ala Glu Thr Trp Cys Asp Arg Glu Leu Tyr Cys Leu Lys
                20                  25                  30

Ala Ser Val Gly Ala Pro Pro Asp Ile Leu Gly Pro Leu Gly Gln Asn
                35                  40                  45

Trp Gly Leu Pro Pro Met Asp Pro His Ile Ile Thr Ala Arg Ala Tyr
                50                  55                  60

Glu Pro Phe Ile Glu Leu Leu Arg Ala Asn Met Gln Asn Cys Gly Ala
65                  70                  75                  80

Leu Arg Ile Asp His Val Met Ser Met Leu Arg Leu Trp Trp Ile Pro
                85                  90                  95

Tyr Arg Glu Thr Ala Asp Gln Gly Ala Tyr Val His Tyr Pro Val Asp
                100                 105                 110

Asp Leu Leu Ser Ile Leu Ala Leu Glu Ser Lys Arg His Arg Cys Met
                115                 120                 125
```

```
Val Ile Gly Glu Asp Leu Gly Thr Val Pro Val Glu Ile Val Gly Lys
    130                 135                 140

Leu Arg Ser Ser Gly Val Tyr Ser Tyr Lys Val Leu Tyr Phe Glu Asn
145                 150                 155                 160

Asp His Glu Lys Thr Phe Arg Ala Pro Lys Ala Tyr Pro Glu Gln Ser
                165                 170                 175

Met Ala Val Ala Ala Thr His Asp Leu Pro Thr Leu Arg Gly Tyr Trp
                180                 185                 190

Glu Cys Gly Asp Leu Thr Leu Gly Lys Thr Leu Gly Leu Tyr Pro Asp
                195                 200                 205

Glu Val Val Leu Arg Gly Leu Tyr Gln Asp Arg Glu Leu Ala Lys Gln
    210                 215                 220

Gly Leu Leu Asp Ala Leu His Lys Tyr Gly Cys Leu Pro Lys Arg Ala
225                 230                 235                 240

Gly His Lys Ala Ser Leu Met Ser Met Thr Pro Thr Leu Asn Arg Gly
                245                 250                 255

Leu Gln Arg Tyr Ile Ala Asp Ser Asn Ser Ala Leu Leu Gly Leu Gln
                260                 265                 270

Pro Glu Asp Trp Leu Asp Met Ala Glu Pro Val Asn Ile Pro Gly Thr
    275                 280                 285

Ser Tyr Gln Tyr Lys Asn Trp Arg Arg Lys Leu Ser Ala Thr Leu Glu
    290                 295                 300

Ser Met Phe Ala Asp Asp Gly Val Asn Lys Leu Leu Lys Asp Leu Asp
305                 310                 315                 320

Arg Arg Arg Arg Ala Ala Ala Lys Lys Lys
                325                 330

(2) INFORMATION FOR SEQ ID NO:4:

(i) SEQUENCE CHARACTERISTICS:
        (A) LENGTH: 323 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Ser Gly Met Lys Leu Gly Ile Tyr Gly Asp Leu Ala Val Asn Ser Ser
1               5                   10                  15

Arg Gly Ser Ala Asp Val Trp Ser Asp Pro Asp Leu Tyr Cys Val Asn
                20                  25                  30

Ala Ser Ile Gly Ala Pro Pro Asp Pro Leu Gly Pro Val Gly Gln Asn
                35                  40                  45

Trp Asn Leu Pro Pro Tyr Asn Pro Thr Val Leu Lys Ala Arg Gly Phe
    50                  55                  60

Ala Pro Phe Ile Asp Met Leu Cys Ala Asn Met Gln Tyr Phe Gly Val
65                  70                  75                  80

Leu Arg Ile Asp His Val Met Gly Leu Phe Arg Leu Trp Trp Ile Pro
                85                  90                  95

Lys Gly Lys Thr Ala Ala Asp Gly Ala Tyr Val His Tyr Pro Phe Asp
                100                 105                 110

Glu Leu Met Ala Ile Leu Ala Ile Glu Ser Val Arg Asn Glu Cys Leu
            115                 120                 125

Ile Ile Gly Glu Asp Leu Gly Thr Val Pro Asp Glu Val Arg Trp Lys
            130                 135                 140
```

```
Leu Asn Glu Phe Gln Ile Phe Ser Tyr Phe Val Leu Tyr Phe Ala Gln
145                 150                 155                 160

Arg Asn Gly Glu Phe Pro Arg Ile Ser Asp Tyr Pro Arg Asn Ala Tyr
                165                 170                 175

Ala Thr Ile Gly Thr His Asp Val Pro Ser Leu Gln Ser Phe Trp His
                180                 185                 190

Cys Arg Asp Leu Glu Leu Phe Asn Gln Leu Gly Ile Leu Asn Gly Glu
            195                 200                 205

Val Leu Lys Gln Lys Tyr Asp Gln Arg Val Met Asp Lys Gln Ala Leu
        210                 215                 220

Leu Asn Ser Leu His Arg Asp Asn Tyr Leu Pro Pro His Tyr Glu Gly
225                 230                 235                 240

Asp Ala Leu Ser Met Ala Met His Asp Tyr Leu Asn Arg Met Ile His
                245                 250                 255

Tyr Tyr Leu Ala Glu Ser Asn Ser Arg Leu Ile Gly Val Gln Leu Glu
            260                 265                 270

Asn Leu Leu Ser Gln Glu Ile Ser Phe Asn Leu Pro Ser Thr Ser Asn
        275                 280                 285

Glu Tyr Pro Asn Trp Cys Lys Leu Ala Gln Pro Leu Ala Phe Ile
290                 295                 300

Phe Ser Asn Glu Ala Leu Lys Thr Phe Phe Val Gln Ile Asn Gln Gly
305                 310                 315                 320

Arg Asn Val
```

(2) INFORMATION FOR SEQ ID NO:5:

(i) SEQUENCE CHARACTERISTICS:
        (A) LENGTH: 298 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Asn His Ile Glu Ile Val Gly Asp Met Pro Ile Tyr Val Ala Glu Asp
1               5                   10                  15

Ser Ser Asp Met Trp Ala Asn Pro His Leu Phe Lys Thr Asp Val Asn
            20                  25                  30

Gly Lys Ala Thr Cys Ile Ala Gly Cys Pro Pro Asp Glu Phe Ser Val
        35                  40                  45

Thr Gly Gln Leu Trp Gly Asn Pro Ile Tyr Asp Trp Glu Ala Met Asp
50                  55                  60

Lys Asp Gly Tyr Lys Trp Trp Ile Glu Arg Leu Arg Glu Ser Phe Lys
65                  70                  75                  80

Ile Tyr Asp Ile Val Arg Ile Asp His Phe Arg Gly Phe Glu Ser Tyr
                85                  90                  95

Trp Glu Ile Pro Ala Gly Ser Asp Thr Ala Ala Pro Gly Glu Trp Val
            100                 105                 110

Lys Gly Pro Gly Tyr Lys Leu Phe Ala Ala Val Lys Glu Glu Leu Gly
        115                 120                 125

Glu Leu Asn Ile Ile Ala Glu Asp Leu Gly Phe Met Thr Asp Glu Val
        130                 135                 140

Ile Glu Leu Arg Glu Arg Thr Gly Phe Pro Gly Met Lys Ile Leu Gln
145                 150                 155                 160

Phe Ala Phe Asn Pro Glu Asp Glu Ser Ile Asp Ser Pro His Leu Ala
                165                 170                 175
```

```
Pro Ala Asn Ser Val Met Tyr Thr Gly Thr His Asp Asn Asn Thr Val
            180                 185                 190

Leu Gly Trp Tyr Arg Asn Glu Ile Asp Asp Ala Thr Arg Glu Tyr Met
            195                 200                 205

Ala Arg Tyr Thr Asn Arg Lys Glu Tyr Glu Thr Val His Ala Met
210                 215                 220

Leu Arg Thr Val Phe Ser Ser Val Ser Phe Met Ala Ile Ala Thr Met
225                 230                 235                 240

Gln Asp Leu Leu Glu Leu Asp Glu Ala Ala Arg Met Asn Phe Pro Ser
            245                 250                 255

Thr Leu Gly Gly Asn Trp Ser Trp Arg Met Thr Glu Asp Gln Leu Thr
            260                 265                 270

Pro Ala Val Glu Glu Gly Leu Leu Asp Leu Thr Thr Ile Tyr Arg Arg
            275                 280                 285

Ile Asn Glu Asn Leu Val Asp Leu Lys Lys
290                 295
```

(2) INFORMATION FOR SEQ ID NO:6:

(i) SEQUENCE CHARACTERISTICS:
        (A) LENGTH: 291 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Lys Gly Ile Ser Ile Met Gly Asp Met Pro Ile Tyr Val Gly Tyr His
1               5                   10                  15

Ser Ala Asp Val Trp Ala Asn Lys Lys Gln Phe Leu Leu Asn Arg Lys
                20                  25                  30

Gly Phe Pro Leu Ile Val Ser Gly Val Pro Pro Asp Ala Phe Ser Glu
            35                  40                  45

Thr Gly Gln Leu Trp Gly Ser Pro Leu Tyr Asp Trp Lys Ala Met Glu
50                  55                  60

Lys Asp Gly Phe Ser Trp Trp Val Arg Arg Ile Gln Arg Ala Thr Asp
65                  70                  75                  80

Leu Phe Asp Glu Phe Arg Ile Asp His Phe Arg Gly Phe Ala Gly Phe
                85                  90                  95

Trp Ala Val Pro Ser Glu Glu Lys Ile Ala Ile Leu Gly Arg Trp Lys
            100                 105                 110

Val Gly Pro Gly Lys Pro Leu Phe Asp Ala Ile Leu Gln Ala Val Gly
            115                 120                 125

Lys Ile Asn Ile Ile Ala Glu Asp Leu Gly Val Ile Thr Glu Asp Val
130                 135                 140

Val Gln Leu Arg Lys Ser Ile Glu Ala Pro Gly Met Ala Val Leu Gln
145                 150                 155                 160

Phe Ala Phe Gly Ser Asp Ala Glu Asn Pro His Leu Pro His Asn His
                165                 170                 175

Glu Gln Asn Gln Val Val Tyr Thr Gly Thr His Asp Asn Asp Thr Ile
            180                 185                 190

Arg Gly Trp Trp Asp Thr Leu Pro Gln Glu Glu Lys Ser Asn Val Leu
            195                 200                 205

Lys Tyr Leu Ser Asn Ile Glu Glu Glu Ile Ser Arg Gly Leu Ile
210                 215                 220
```

-continued

```
Glu Gly Ala Val Ser Ser Val Ala Arg Ile Ala Ile Ile Pro Met Gln
225                 230                 235                 240

Asp Val Leu Gly Leu Gly Ser Asp Ser Arg Met Asn Ile Pro Ala Thr
                245                 250                 255

Gln Phe Gly Asn Trp Ser Trp Arg Ile Pro Ser Ser Thr Ser Phe Asp
            260                 265                 270

Asn Leu Asp Ala Glu Ala Lys Lys Leu Arg Asp Ile Leu Ala Thr Tyr
        275                 280                 285

Gly Arg Leu
    290
```